United States Patent

Nemser et al.

[11] Patent Number: 5,876,604
[45] Date of Patent: Mar. 2, 1999

[54] METHOD OF GASIFYING OR DEGASIFYING A LIQUID

[75] Inventors: Stuart Marshall Nemser, Wilmington, Del.; Jay Olpin, Jefferson, Md.

[73] Assignee: Compact Membrane Systems, Inc, Wilmington, Del.

[21] Appl. No.: 735,922

[22] Filed: Oct. 24, 1996

[51] Int. Cl.[6] .................................................... B01D 11/00
[52] U.S. Cl. .......................... 210/634; 210/637; 210/640; 210/645; 210/321.6; 435/2; 435/325; 435/372; 435/382; 435/385; 435/410; 435/243
[58] Field of Search .................................. 210/634, 637, 210/640, 645, 321.6; 435/2, 325, 372, 382, 385, 410, 243

[56] References Cited

U.S. PATENT DOCUMENTS

| | | | |
|---|---|---|---|
| 4,230,463 | 10/1980 | Henis et al. | 55/16 |
| 4,844,871 | 7/1989 | Polaschegg | 422/81 |
| 4,938,778 | 7/1990 | Ohyabu et al. | 623/66 |
| 5,051,114 | 9/1991 | Nemser et al. | 55/16 |
| 5,116,650 | 5/1992 | Bowser | 428/34.2 |
| 5,238,471 | 8/1993 | Blanchet-Fincher | 96/13 |
| 5,258,202 | 11/1993 | Pellegrino et al. | 427/235 |
| 5,523,118 | 6/1996 | Williams | 427/208.8 |
| 5,554,414 | 9/1996 | Moya et al. | 427/244 |

FOREIGN PATENT DOCUMENTS

| | | |
|---|---|---|
| 0649676 | 4/1994 | European Pat. Off. . |
| 0641194 | 5/1995 | European Pat. Off. . |
| WO 90/15662 | 12/1990 | WIPO . |

OTHER PUBLICATIONS

Lund, L.W., et al., Gas permeability of hollow fiber membranes in a gas–liquid system, *Journal of Membrane Science*, 117 (1996) 207–219.

Nemser, S., Applications of Membranes in Industry Glassy Fluoropolymer Membranes, 21st Aharon Katzir–Katchalsky Conference, Rehovot, Israel, Sep. 5–8, 1993.

Nemser, S., "Graph I" presentation at University of Pittsburgh, Pittsburgh, Pennsylvania, Feb. 27, 1996.

Pinnau et al: J. membrane Sci., vol. 109, pp. 125–133. 1996.

*Primary Examiner*—Ponnathapura Achutamurthy
*Attorney, Agent, or Firm*—Jeffrey C. Lew

[57] ABSTRACT

A method of adding or removing a gas to or from a solution of the gas in a liquid involves transferring the gas between the liquid and another fluid through a membrane unit. The membrane unit includes a membrane which is (i) substantially impermeable to the solvent and having a permeability to oxygen of at least 100 barrers; (ii) formed from an amorphous copolymer of perfluoro-2,2-dimethyl-1,3-dioxole; and (iii) is maintained at a temperature below the glass transition temperature of the copolymer. The fluid can be another liquid or a gas. The novel method provides very high rates of gas transmission between liquids and permits gasifying liquids without resort to sparging bubbles through the liquid. The method thus can gasify liquid with superior efficiency and without excessive agitation due to bubbling. These features result in economy of gas consumption and reduced need for gas recovery equipment, and when used in connection with a toxic or organic gaseous component, reduced requirements for additional pollution control equipment. The membrane material is resistant to fouling by liquids, and especially, by bioreactor mass. Hence, the novel method can remain in service for long duration without substantially diminished performance. Utilities for the novel method include purifying drinking water through ozonolysis, oxygenating bioreactors and blood; oxidizing volatile organic compounds in water; adding gaseous reactants to liquid chemical reactions and supplying oxygen to and removing volatile pollutants from waste water.

32 Claims, 4 Drawing Sheets

METHOD OF GASIFYING OR DEGASIFYING A LIQUID

FIELD OF THE INVENTION

This invention relates to a method of transporting a gas to or from a solution of the gas in a liquid through a substantially liquid impermeable and gas permeable polymer membrane.

BACKGROUND AND SUMMARY OF THE INVENTION

The ability to transport a gas to or from the dissolved state in a liquid has many uses. These include purifying drinking water through ozonolysis, oxygenating bioreactors and restoring oxygen to blood; oxidizing volatile organic compounds in water; adding gaseous reactants to liquid chemical reactions and supplying oxygen and removing volatile pollutants from waste water to name a few.

Generally in conventional methods of gasifying a liquid, the gas is bubbled directly into the liquid. Devices such as perforated or fritted sparging tubes and nozzles may be used to reduce the size of the bubbles. Although bubble size reduction improves the rate of mass transfer by raising the gas-liquid interfacial area per unit volume, bubbling is highly inefficient for gasifying a liquid and has additional shortcomings. Due to contact inefficiency, bubbling normally requires adding more than the required stoichiometric amount of gas. Excess gas must be discarded or recovered. Furthermore, the discarded gas frequently may be an undesirable pollutant and before it can be emitted to the environment, the gas must be treated. At the very least, discarding excess gas adds material cost without adding value to the primary product. Recovery of excess gas also complicates the product manufacturing process which adds still more cost. Process complications introduced by the recovery of excess gas can include stripping entrained liquid or upstream contaminants from the exhaust gas and measuring the concentration of such liquid and contaminants in the recovered gas. Liquid entrained in the excess gas can contain dissolved solids which tend to precipitate in the gas recovery equipment. Removal of these solids further adds to the difficulty of recovering the excess gas.

Bubbling also can be incompatible with the process for which the liquid is being gasified. For example, in a bioreactor, the agitation caused by bubbling can interfere with growth of fragile cells or destroy the cells. Gas bubbles entrained in oxygenated blood can be dangerous to an individual and normally should be eliminated completely.

Gas permeable polymer membranes might present an attractive technology for conducting mass transfer of gases. U.S. Pat. No. 5,051,114 to S. Nemser, issued Sep. 24, 1991, which is incorporated herein by reference, teaches the use of permeable polymer membranes for enriching or separating a gaseous organic compound in a gas or a gas mixture. However, most gas permeable membranes are not suited to transporting gas to or from a liquid. If the membrane is perforated or porous, gas can pass through the membrane too quickly and bubble into the liquid with the attendant disadvantages noted above. Also, the liquid can leak through the perforations or pores to contaminate the gas. Additionally the liquid and/or solids which might be present can clog the pores to reduce gas transfer.

Most nonporous polymer permeable membranes present too great a barrier to gas transfer for practical gasifying or degasifying a liquid. Low free volume gas permeable membranes of nonporous polymers have wholly inadequate gas permeability. Other known high free volume, nonporous polymer, gas permeable membranes are not acceptable for transporting gas to or from a liquid. Polytrimethylsilylpropyne ("PTMSP") is one of few known high free volume, nonporous polymers potentially suitable for gas permeable membranes. When used to gasify liquids, PTMSP membranes yield initially substantial but rapidly and dramatically declining gas flux. Although there may be other explanations, it is understood that this flow rate reduction is caused by liquid filling the free volume and thereby obstructing gas flow. Furthermore, certain corrosive gases, such as chlorine and ozone, chemically attack PTMSP. Silicone rubber is another nonporous, polymer with potential use in gas permeable membranes. Unfortunately, silicone rubber cannot be fabricated easily into thin membranes or thin coatings on high surface area substrates. Consequently, silicone rubber membranes usually include a thick polymer layer which constrains gas flow to relatively low rates.

It is very desirable to provide a nonporous, permeable polymer membrane capable of transporting gas to and from the dissolved state in a liquid at high flow rates. According to the present invention it has been discovered that nonporous gas permeable membranes formed from certain copolymers of perfluoro-2,2-dimethyl-1,3-dioxole ("PDD") allow gas transfer into and out of a liquid at high rate. Furthermore, the high gas flux can be maintained for extended duration.

The present invention thus provides a method of transferring a gaseous component between two fluids having different partial pressures of the gaseous component, and wherein at least one of the two fluids is a liquid, the method comprising:

contacting one of the two fluids with a first side of a two-sided, membrane unit, the membrane unit including a membrane (i) being substantially impermeable to the liquid and having a permeability to oxygen of at least 100 barrers; (ii) formed from an amorphous copolymer of perfluoro-2,2-dimethyl-1,3-dioxole; and (iii) being at a temperature below the glass transition temperature of the amorphous copolymer; and simultaneously contacting the second side of the two-sided, membrane unit with the other of the two fluids.

In one aspect this invention further provides a method of oxygenating blood having a low blood oxygen partial pressure, the method comprising:

contacting blood with a first side of a two-sided, membrane unit, the membrane unit including a membrane (i) being substantially impermeable to blood and having a permeability to oxygen of at least 100 barrers; (ii) formed from an amorphous copolymer of perfluoro-2,2-dimethyl-1,3-dioxole; and (iii) being at a temperature below the glass transition temperature of the copolymer; and simultaneously contacting the second side of the two-sided, membrane unit with a gaseous mixture containing oxygen at a partial pressure higher than the low blood oxygen partial pressure.

In another aspect pertaining specifically to a bioreactor, the present invention additionally provides a method of oxygenating a liquid reaction medium containing living cells and having a low oxygen partial pressure, the method comprising:

contacting the liquid reaction medium with a first side of a two-sided, membrane unit, the membrane unit including a membrane (i) being substantially impermeable to the liquid reaction medium and having a permeability to oxygen of at least 100 barrers; (ii) formed from an amorphous copolymer of perfluoro-2,2-dimethyl-1,3-dioxole; and (iii) being at a temperature below the glass transition temperature of the copolymer; and simultaneously contacting the second side of the two-sided, membrane unit with a gaseous mixture containing oxygen at a partial pressure higher than the low oxygen partial pressure.

DETAILED DESCRIPTION

In a broad sense, the present invention involves a method of transporting a gaseous component through a substantially liquid impermeable and gas permeable membrane between two fluids, at least one of which is a liquid. With respect to the liquid, the term "gasify" is used herein to mean that the concentration of the gaseous component increases in the liquid. Conversely, the term "degasify" means that the gaseous component is transported out of the liquid to the other fluid.

The gaseous component generally is a low molecular weight chemical substance which exists in the gaseous state, i.e., as a gas at atmospheric pressure and about 25° C. The gaseous component can be a pure substance or a mixture. It can be any of a broad range of chemical species. Representative gaseous components include elemental gases such as helium, hydrogen, neon, nitrogen, chlorine, argon, oxygen, krypton and xenon; hydrocarbons such as methane, ethylene, ethane, acetylene, propane, propylene, cyclopropane, butane and butylene; halocarbons or halohydrocarbons such as dichlorodifluoromethane, methylene chloride, and methyl chloride; and miscellaneous industrial and environmental gases such as nitrous oxide, carbon dioxide, ozone, hydrogen sulfide, ammonia, sulfur dioxide, carbon monoxide, phosgene and any mixture of any of them. Oxygen is a preferred non-mixture gaseous component. Oxygen/ozone, oxygen/nitrogen, oxygen/nitrogen/ozone are preferred mixtures; and air and air/ozone are more preferred.

It is convenient to refer to the fluids on opposite sides of the gas permeable membrane as the source fluid and destination fluid with respect to the direction of migration of the gaseous component. At least one of the two fluids is in the liquid state. That is, the fluid on at least one side of the membrane is a liquid. The fluid on the other side can be a gas or a liquid. The source fluid, the destination fluid or both can be liquid. An important feature of the novel method is that the gaseous component is not present in the gaseous state in the liquid in substantial amount. Instead, the gaseous component can be dissolved in the liquid or it can react quickly with the liquid or other substances in the liquid. Consequently, the liquid can be considered to act as a solvent for the gaseous component. Provided that the gaseous component is present in the liquid below saturation, the gaseous component-containing fluid will remain liquid and no free gas will appear, i.e., bubbling will not occur.

The liquid can be a single compound or a mixture. A wide variety of liquids such as aqueous and nonaqueous solvents can be used according to the present invention. Liquids can include water; alcohols; ethers; ketones; esters; and combinations of these. Representative alcohols include ethanol, butanol, and ethylene glycol. Representative ethers include dimethylether, diethylether and anisole. Representative ketones include acetone, ethylmethylketone and diethylketone. Representative esters include methylacetate, methylpropionate and ethyl acetate. Representative combinations include cellosolve; ethylcellosolve; acetylcarbinol; cellosolve acetate; polyethylene ether glycol, methoxyacetone; methylmethoxy acetate and methylketo butyrate. Water is a preferred liquid for use in the present invention.

The membrane is formed from an amorphous copolymer of a certain perfluorinated dioxole monomer, namely perfluoro-2,2-dimethyl-1,3-dioxole ("PDD"). In some preferred embodiments, the copolymer is copolymerized PDD and at least one monomer selected from the group consisting of tetrafluoroethylene ("TFE"), perfluoromethyl vinyl ether, vinylidene fluoride and chlorotrifluoroethylene. In other preferred embodiments, the copolymer is a dipolymer of PDD and a complementary amount of TFE, especially such a polymer containing 50–95 mole % of PDD. Examples of dipolymers are described in further detail in U.S. Pat. Nos. 4,754,009 of E. N. Squire, which issued on Jun. 28, 1988; and 4,530,569 of E. N. Squire, which issued on Jul. 23, 1985. Perfluorinated dioxole monomers are disclosed in U.S. Pat. No. 4,565,855 of B. C. Anderson, D. C. England and P. R. Resnick, which issued Jan. 21, 1986. The disclosures of all of these U.S. patents are hereby incorporated herein by reference.

Figure 1:
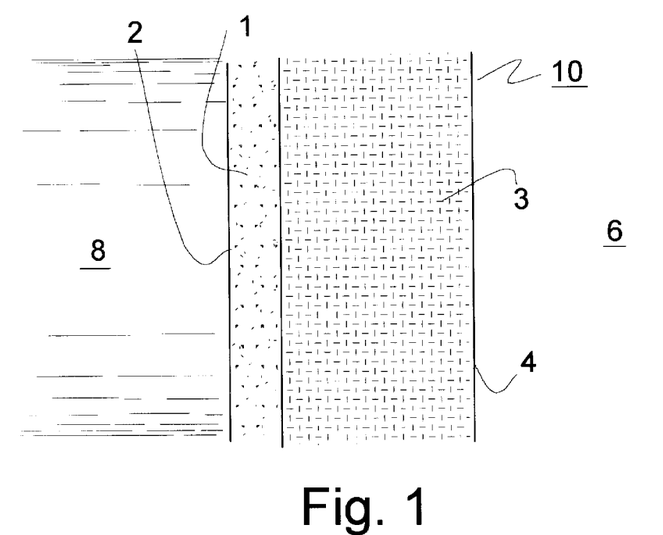
FIG. 1 is a section view of a membrane unit according to one embodiment of the present invention.

The amorphous copolymer can be characterized by its glass transition temperature ("$T_g$"). Glass transition temperature property of a polymer is understood in the art. It is the temperature at which the copolymer changes from a brittle, vitreous or glassy state to a rubbery or plastic state. The glass transition temperature of the amorphous copolymer will depend on the composition of the specific copolymer of the membrane, especially the amount of TFE or other comonomer that may be present. Examples of $T_g$ are shown in FIG. 1 of the aforementioned U.S. Pat. No. 4,754,009 of E. N. Squire as ranging from about 260° C. for dipolymers with 15% tetrafluoroethylene comonomer down to less than 100° C. for the dipolymers containing at least 60 mole % tetrafluoroethylene. It can be readily appreciated that perfluoro-2,2-dimethyl-1,3-dioxole copolymers according to this invention can be tailored to provide sufficiently high $T_g$ that a membrane of such composition can withstand exposure to steam temperatures. Hence, membranes of this invention can be made steam sterilizable and thereby suitable for various uses requiring sterile materials, especially those involving biological materials. Preferably, the glass transition temperature of the amorphous copolymer should be at least 115° C.

The PDD copolymer makes the gas permeable membrane of the novel method uniquely and particularly well suited to accomplish the transport of a gaseous component to or from a liquid. Firstly, the amorphous copolymer is both hydrophobic and organophobic. This property makes the membrane material substantially impermeable to a wide variety of liquids. Impermeability to liquid importantly prevents liquid leakage between the fluids, a condition sometimes referred to as "break-through" or "wetting out" of the membrane. The term "substantially impermeable" means that the liquid fluid will not break through the membrane even when a significant positive pressure differential is applied across the membrane. For example, a 50/50 isopropanol/water solution at up to about 207 KPa (30 psig) pressure will not break through a membrane of PDD copolymer into an atmospheric pressure, gas-filled chamber. Such break-through ordinarily can be detected by visual inspection. The extreme hydrophobicity and organophobicity of the PDD copolymer also makes the gas permeable membrane not more than negligibly soluble or swellable in a wide range of liquids. This characteristic assures the preservation of the structural integrity and dimensional stability of the membrane while in contact with many liquid compositions.

Secondly, the amorphous copolymer can be applied readily in thin layers on high surface area per unit volume substrates, such as the inside and/or outside surfaces of hollow fibers. The amorphous copolymer used in the present invention has very good permeability. For example, PDD/TFE copolymer membranes exhibit a permeability for oxygen of at least 100 barrers, especially at least 200 barrers and in particular at least 500 barrers. Certain conventional gas permeable membrane materials may have comparable permeabilities, however, they cannot easily be formed into thin layers on high surface area per unit volume substrates. Normally, these materials are formed into flat sheet membranes. Because the PDD copolymers can be thinly coated onto structures such as hollow fibers, the membranes can be packaged in modules which have significantly higher density of surface area available for mass transfer than an equivalent volume of conventional, flat sheet gas permeable membranes. Consequently, the present method provides superior gas flux into or out of liquids than conventional methods due to the combination of high gas permeability and the ability to assemble very compact modules using high surface area substrates with thin coatings of permeable membrane.

Thirdly, PDD copolymer membranes additionally possess a selectivity among gaseous components, most notably a selectivity of oxygen over nitrogen. Preferably the oxygen/nitrogen selectivity will be at least about 1.5:1. The gas selectivity of the PDD copolymer membranes can be exploited conveniently to test the membranes for coating defects. The need for PDD copolymer to completely coat the substrate is accentuated in certain embodiments of the present invention which involve an extremely thin layer of amorphous copolymer coated on a high surface area per unit volume substrate. The detection of defects might otherwise be difficult because the copolymer layer is so thin. However, the membrane can be evaluated easily for absence of holes, for example, by exposing one side of the membrane to a known, constant pressure, mixture of selected gases and analyzing the atmosphere on the other side for concentration of the gases consistent with the selectivity of the membrane composition.

Fourthly, the PDD copolymer membrane of this invention is very resistant to fouling by liquids. Accordingly, the membrane has the advantageous ability to sustain for extensive duration high gas flux to or from a liquid with which the membrane is in contact. Furthermore, the high gas flow rate stability will be largely unaffected by the presence of contaminants in the fluids. Therefore, the liquid in contact with the membrane may exist in a wide range of purity. For example, the novel method can be used to transport a gaseous component to or from water of any grade ranging from reagent quality, demineralized water to process quality water, such as brackish water, salt water, and environmental waste water containing various contaminants. Moreover, the excellent gas flux stability makes the present invention particularly useful for gasifying or degasifying biological fluids. Biological fluids include human and other animal natural body fluids such as blood, and other natural, synthetic or combined liquid media for cell culturing. Such fluids typically contain cells and other microorganisms which tend to adhere to and grow on many substrate materials. PDD copolymer membranes to a great extent can resist adhesion and maintain good gas flow in biological fluid systems.

Preferred utilities for the present invention include ozonating sanitary or industrial waste water to remove undesirable microorganisms and organics; remediation by oxygenating natural streams, ponds and waterways depleted of oxygen by industrial waste contamination or farm land run off; oxygenating water in tanks and ponds for purposes of aquaculture; and depleting oxygen in reactors for anaerobic reactions or boiler water feed. The novel method is particularly preferred for use in bioreactor systems. The term "bioreactor" is used herein to mean reaction equipment for carrying out processes which incorporate living organisms, such as cells and bacteria, as the product of such processes or as agents for producing a chemical product. The oxygenation of blood and the oxygenation of cell culture media to enhance cell growth are examples of bioreactor system operations.

The gas permeable membrane can be a monolithic film. To maintain structural integrity, such a film should be thick enough to withstand pressure differences between the fluids. However, to maximize the rate of gas transmission the membrane should be thin. Preferably the membrane of this invention includes a thin layer or coating of PDD copolymer. The layer or coating is placed on a porous substrate which provides structural strength and minimal flow resistance. The composite of amorphous copolymer and porous substrate thus forms a membrane unit. The term "membrane unit" is used occasionally herein to mean either a gas permeable membrane or such membrane affixed coextensively over the gas transfer area with a substrate. Useful membrane units include, but are not limited to, thin film composite films and composite hollow fibers. The structure of the substrate should be designed to have substantial porosity so as not to impede the flow of the gaseous component. The porosity of the substrate can be effected by perforations or microscopic pores. Representative porous substrates include a rigid, perforated sheet; a porous woven fabric; a monolithic microporous polymer film and a microporous, hollow fiber. To maximize gas flux, the thickness of the PDD copolymer membrane preferably should be less than about 10 $\mu$m, and more preferably, less than about 1 $\mu$m.

A 1 $\mu$m thickness coating on the outside of a 250 $\mu$m outside diameter polypropylene hollow fiber yields a mass transfer area per unit volume of 8.2 $cm^2/cm^3$ with a fiber packing density of 20%. In contrast, silicone rubber cannot be easily coated on hollow fibers. The typical area density for a flat sheet geometry membrane structure is only 1.1 $cm^2/cm^3$ or one eighth of packed hollow fibers. As shown in the examples following, below, the gas transmission rate per unit area through membrane structures based on copolymers of perfluoro-2,2-dimethyl-3,1-dioxole are approximately three to four times that of conventional materials such as silicone rubber. Hence, the methods of the present invention provide about 25–30 times the volumetric efficiency of gas transmission to liquid of conventional membranes (i.e., about 3.5 flux enhancement factor ×8 area density improvement factor).

The nature of the membrane unit can be appreciated with reference to FIG. 1. The membrane unit 10 includes a layer of amorphous copolymer membrane 1 deposited on a porous substrate 3. The membrane unit characteristically has two sides 2 and 4, each in contact with a different one of the two fluids. Gaseous component in source fluid 6 will migrate through the support structure to dissolve in destination fluid 8. As previously mentioned, copolymers of PDD are very inert to liquids, i.e., the copolymer generally does not clog with non-gaseous components of the fluid. In addition, mass transfer of gases is generally slower in both liquids and porous substrate material than within a gas phase. Therefore, to achieve and maintain stability of maximum flux, the amorphous copolymer membrane 1 preferably should contact one of the fluids 8 which is a liquid. It is acceptable to reverse position of fluids 6 and 8, i.e. so that membrane unit side 2 contacts the gaseous fluid and side 4 contacts the liquid, however, gas flux could be reduced because of resistance to mass transfer of dissolved gaseous component through the substrate.

Figure 2:
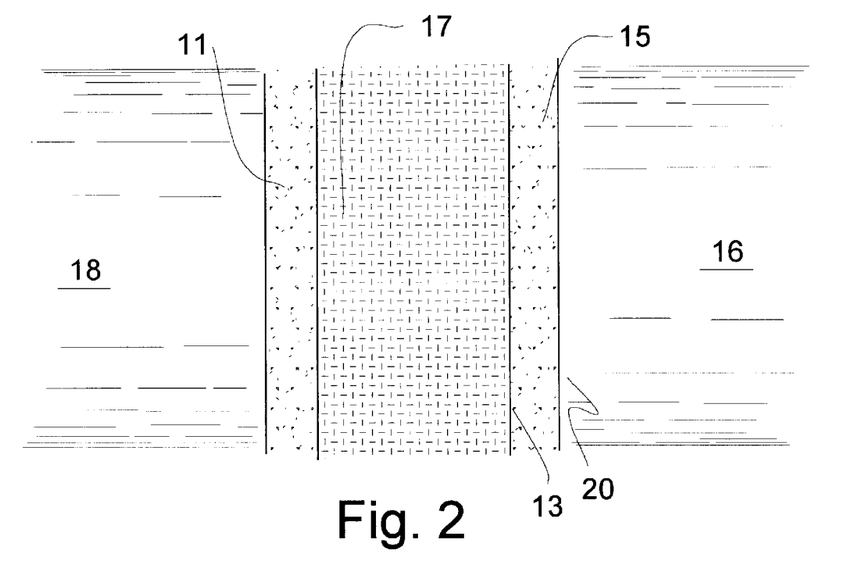
FIG. 2 is a section view of a membrane unit according to another embodiment of the present invention.

FIG. 2 shows a membrane unit 20 well suited to liquid-to-liquid gas transfers, i.e., in which a gas is transferred between two liquids 16 and 18. Such a membrane unit includes an optional, second coating 15 of amorphous copolymer. The second coating can be affixed to the face 13 of the substrate material 17 nonadjacent to first coating 11. That is, the membrane unit is a sandwich configuration comprising a porous substrate 17 between two amorphous copolymer membranes, 11 and 15. The amorphous copolymers of the two coatings can be the same or different.

The membrane units of the present invention may be manufactured by a variety of methods known to those skilled in the art, including coating techniques such as dipping, spraying, painting and applying by doctor blade. PDD copolymers are amenable to solvent or melt processing, while other fluoropolymers tend to be only melt processible. The solvent processing capability permits PDD copolymers to be coated in very thin films on high surface area per unit volume substrates. Consequently, the present invention can effect high gas transfer rates that are difficult to match through membrane units produced by melt processing techniques.

Broadly described, the mass transfer through the membrane will be driven by a difference between partial pressures of the gaseous component in the two fluids. Generally, the gaseous component will migrate across the amorphous copolymer membrane from the source fluid in which it is present at high partial pressure to the destination fluid in which it is at lower partial pressure. For example, oxygen deficient water can be oxygenated by contacting one side of a membrane unit according to this invention with the water and contacting the second side with air. Raising the partial pressure of the gaseous component in the source fluid normally increases the driving force for migration through the membrane. Hence, in this example, the partial pressure of oxygen in the water can be increased further, by changing the fluid on the second side to mixtures of increased oxygen partial pressure ranging up to substantially pure oxygen. Alternatively, the dissolved oxygen partial pressure can be increased by raising the absolute pressure of the source fluid, or by combining increased oxygen partial pressure and raised source fluid absolute pressure.

The method of gas transfer through a gas permeable membrane according to the present method provides great flexibility in choosing operating conditions to optimize the rate of transfer to or from a liquid. That is, the unique combination of substantial liquid impermeability and high gas permeability of the PDD copolymer membrane permits operating conditions for each of the two fluids to be set independently of the other. By way of example, it can be appreciated by one of ordinary skill in the art, that a liquid has greater capacity to retain a gaseous component in the dissolved state at higher liquid pressure. Therefore, a greater amount of dissolved gaseous component can be introduced into a liquid without producing gas bubbles by raising liquid pressure. Because of the notably high resistance to liquid break-through of PDD copolymers mentioned earlier, a liquid in contact with a PDD copolymer membrane can be successfully held at relatively high pressure to improve gas solubility. In the process of gasifying a destination liquid with a source gas on the opposite side of the membrane, the pressure of the liquid can exceed the pressure of the source gas without substantial risk of leaking liquid into the source gas. For such a process, the difference of liquid pressure over gas pressure can be at least 13.8 KPa (2 psi), preferably at least 34.5 KPa (5 psi), and more preferably, at least 68.9 KPa (10 psi). The pressure of the source fluid and the destination fluid each independently can be slightly below, about equal to, or above atmospheric pressure. As will be appreciated by persons skilled in the art, the migration of gaseous component through the membrane can be driven solely by a difference of partial pressures of the component in the source and destination fluids. Thus it is desirable to maintain the liquid at superatmospheric pressure to maximize gas solubility.

The novel method will usually be operated at about ambient temperature, but may be at higher temperatures. However, the membranes should be used at a temperature below the glass transition temperature, and especially at least 30° C. below the glass transition temperature of the amorphous copolymer used to form the membrane. As previously explained, PDD copolymers can have exceptionally high $T_g$. Hence, the amorphous copolymer membranes used in the method of the present invention are capable of being utilized at elevated temperatures, including in some embodiments at temperatures above 100° C. Of course, the operating temperature should be maintained below the boiling point of the liquid to avoid gas bubbling. The method of the present invention may be operated at relatively low temperatures, e.g., about 10° C.

The examples hereinafter show that the membranes according to the present invention are capable of gasifying and degasifying liquids at very high flux of gaseous component. These examples further demonstrate the stability of mass transfer rate of these membranes in liquid gasifying service. That is, the high flux of gaseous component into and from a liquid can be sustained for extended duration. These features make the novel methods for gasifying and degasifying liquids of great practical significance.

Figure 6:
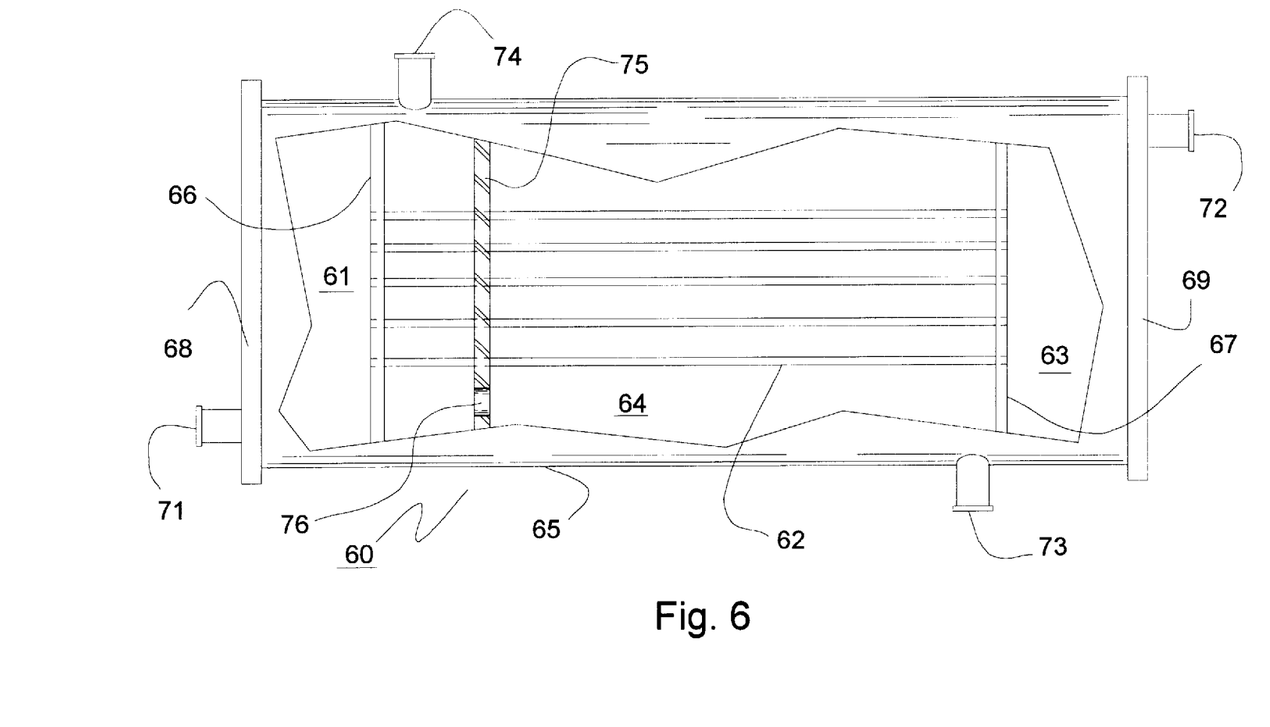
FIG. 6 is a partial section view of a preferred permeator module according to the present invention.

A preferred apparatus for implementation of the novel gasifying or degasifying method is illustrated schematically in FIG. 6. The apparatus shown includes a generally cylindrical permeator module 60 equipped with a plurality of membrane units 62 disposed within a shell side cavity 64 defined by the inside surface of wall 65 of the module, inlet tube sheet 66 and outlet tube sheet 67. The term "permeator module" is used herein to mean an apparatus which includes a plurality of membrane units generally within a common housing and which units are adapted, as in a manifolded configuration, to cooperatively function with a single first fluid stream and a single second fluid stream. The spaces between end plates 68 and 69 and inlet and outlet tube sheets further define inlet and outlet plenums 61 and 63, respectively. Each membrane unit is a generally tubular structure including a hollow fiber substrate with a thin coating of amorphous copolymer over the complete exterior surface of the fiber. Ends of the membrane units terminate at the inlet and outlet tube sheets in the manner that the space within the hollow fibers is in fluid communication with the inlet and outlet plenums. The space inside the permeator module within the inlet and outlet plenums and inside the hollow fibers may be designated as the "tube side" of the module. The membrane unit ends are sealed to the tube sheets so that the space within the fibers is isolated from the shell side cavity 64. The permeator module is further equipped with first fluid inlet and outlet ports 71 and 72, respectively. First fluid inlet port 71 is mounted on end plate 68 and opens through the end plate in fluid communication with inlet plenum 61. First fluid outlet port 72 is mounted on end plate 69 and opens through the end plate in fluid communication with outlet plenum 63. Second fluid inlet port 73 and second fluid outlet port 74 are mounted on the shell of the permeator module and open through the wall 65 in fluid communication with the shell side cavity 64. In the illustrated embodiment, second fluid inlet and outlet ports are shown at opposite ends of the permeator module. The shell side cavity can optionally include one or more internal baffles 75, only one of which is shown in section view, which provide structural support for the membrane units. The baffles will contain openings 76, only one of which is shown, adapted to create a continuous, maze-like path between second fluid inlet and outlet ports. The membrane units can be grouped in bundles comprising multiple units and a permeator module can include a plurality of bundles.

In use, a first fluid, for example a gas mixture including a permeating gaseous component, can be caused to flow through the tube side. A source of the gas mixture is connected to first fluid inlet port and the gas mixture is permitted to enter inlet plenum 61, pass through the interior of hollow fibers 62, discharge to outlet plenum 63 and exhaust through first fluid outlet port 72 to a collection reservoir. Second fluid can be introduced through second fluid inlet port 73 and pumped through the shell side cavity around the membrane units and through the baffle openings to ultimately reach second fluid outlet port 74 for collection. In the illustrated embodiment in which the outside surfaces of the hollow fibers are coated with amorphous copolymer, preferably the tube side (first) fluid will be a gas and the shell side (second) fluid will be a liquid. It can be seen that the permeating gaseous component will migrate through the coating of amorphous copolymer between first and second fluids.

It can readily be appreciated that many variations in the modes of operation, number, shape and placement of permeator module elements are suitable for use in the present invention. Variations to the embodiment shown in FIG. 6 which are contemplated as falling within the breadth of the present invention include, for example, (a) coating the amorphous copolymer coating on the interior surface of the hollow fiber or on both interior and exterior surfaces; and (b) conducting the liquid through the tube side and causing a gas or another liquid to flow through the shell side. As stated elsewhere herein, the liquid state fluid preferably will be in contact with the amorphous copolymer side of the membrane unit. Accordingly, when the liquid flows through the tube side, preferably the inside of the hollow fibers will be coated with the amorphous copolymer. Conversely, as in the embodiment illustrated in FIG. 6, the coating will be on the outside surface of the fibers when the liquid is on the shell side of the permeator module.

In another contemplated embodiment, one or more fluid ports can be capped closed. For example the first fluid port can be shut. This "dead-heading of the tube side fluid, tends to cause the tube side fluid pressure to equilibrate with the pressure of the fluid source. In still another embodiment, the tube assembly, i.e., the fluid inlet port, inlet plenum, tubes, outlet plenum and outlet port, can be adapted without the shell. The sub-unit can be immersed in fluid in a process or storage container to gasify or degasify that fluid without the need to pump the fluid through a shell side of the module.

This invention is now illustrated by examples of certain representative embodiments thereof, wherein all parts, proportions and percentages are by weight unless otherwise indicated. Unless otherwise stated or the contrary is evident from context, all pressures referred to herein are relative to atmospheric pressure.

EXAMPLES

Example 1–13

A dipolymer of 85 mole % perfluoro-2,2-dimethyl-1,3-dioxole and 15 mole % tetrafluoroethylene (hereinafter, "Polymer A") was coated onto the following three types of hollow fiber supplied by Spectrum Microgon (Laguna Hills, Calif.):

"Substrate A": Cellulose ester hollow fiber of 800 $\mu$m outer diameter, 600 $\mu$m inner diameter, and 0.10 $\mu$m pore size;

"Substrate B": Polysulfone hollow fiber of 660 $\mu$m outer diameter, 500 $\mu$m inner diameter, and 50,000 molecular weight cut off("MWCO") pore size; and "Substrate C": Polypropylene hollow fiber of 240 $\mu$m outer diameter, 200 $\mu$m inner diameter, and 0.05 $\mu$m pore size.

The hollow fibers were coated on either the inside or outside surfaces with coatings of thicknesses stated in Table I. Coated fibers were mounted in a permeator module substantially as in FIG. 6 having effective surface areas as indicated in the table. The oxygen/nitrogen selectivity ratios of the coated fibers were measured in accordance with the procedures described in U.S. Pat. No. 5,051,114. As can be seen from Table I, all the selectivity ratios were sufficiently above 1.4 to confirm that the coating was fully intact over substantially all of the hollow fiber substrate surfaces.

Measurement of thickness of Polymer A coating on the hollow fiber substrates involved capping the first fluid outlet port and the second fluid inlet port and measuring the permeation rate of a gas across the modular membrane units at known conditions. By comparing the permeation rates to those of flat sheets of Polymer A of known thickness of about 25–50 $\mu$n, the average thicknesses of the coated fibers were calculated.

TABLE I

| | Support Material | Coating Location | Area (cm$^2$) | Thickness ($\mu$m) | Selectivity $O_2/N_2$ |
|---|---|---|---|---|---|
| Ex. 1 | Cellulose Ester | Outside | 50 | 0.7 | 1.7 |
| Ex. 2 | Cellulose Ester | Outside | 50 | 0.9 | 1.7 |
| Ex. 3 | Cellulose Ester | Outside | 50 | 1.2 | 1.7 |
| Ex. 4 | Cellulose Ester | Inside | 50 | 1.5 | 1.7 |

TABLE I-continued

|  | Support Material | Coating Location | Area (cm$^2$) | Thickness ($\mu$m) | Selectivity O$_2$/N$_2$ |
|---|---|---|---|---|---|
| Ex. 5 | Polysulfone | Outside | 22 | 1.9 | 1.5 |
| Ex. 6 | Polysulfone | Inside | 680 | 0.2 | 1.7 |
| Ex. 7 | Polypropylene | Outside | 63 | 0.8 | 1.8 |
| Ex. 8 | Polypropylene | Outside | 250 | 0.9 | 1.7 |
| Ex. 9 | Polypropylene | Outside | 250 | 0.9 | 1.9 |
| Ex. 10 | Polypropylene | Outside | 850 | 0.6 | 1.7 |
| Ex. 11 | Polypropylene | Inside | 200 | 0.5 | 1.8 |
| Ex. 12 | Polypropylene | Inside | 1000 | 1.4 | 1.9 |
| Ex. 13 | Polypropylene | Inside | 1000 | 1.0 | 1.8 |

These examples show that perfluoro-2,2-dimethyl-1,3-dioxole amorphous copolymer can be coated as thin films on hollow fibers suitable for liquid gasification/degasification service.

Examples 14–16 and Comparative Examples 1–3

A clear shell permeator module substantially as shown in FIG. 6 was prepared using certain polypropylene hollow fibers coated on the outside with a 2–6 $\mu$m layer of Polymer A. A solution of 50/50 isopropanol("IPA")/water was pumped through the shell side of the permeator module. The tube side was vented to ambient atmosphere.

The IPA solution pressure was raised until solution broke through the membrane unit as indicated by visual observation of liquid in the tube side space. The oxygen/nitrogen selectivity of the permeator module was determined according to the procedure cited in Examples 1–13. The pressures of break-through onset of various samples having an assortment of oxygen/nitrogen selectivities were determined and recorded as shown in Table II. The test also was performed on an uncoated polypropylene hollow fiber.

TABLE II

| Example | Material | O$_2$/N$_2$ Selectivity | Breakthrough Press. Kpa (psig) |
|---|---|---|---|
| Ex. 14 | Substrate C | 2.0 | >1240 (180)* |
| Ex. 15 | Substrate D** | 1.8 | 448 (65) |
| Ex. 16 | Substrate C | 1.7 | 413 (60) |
| Comp Ex. 1 | Substrate D | 1.4 | 172 (25) |
| Comp Ex 2 | Substrate D | 1.2 | 172 (25) |
| Comp Ex 3 | Uncoated Substrate D | 0.9 | 34.5 (5) |

*breakthrough exceeded 1.24 MPa (180 psig) limit of test equipment
**200 $\mu$m I.D./250 $\mu$m O.D. 0.05 $\mu$m pore size polypropylene hollow fiber from Hoechst Celanese.

IPA solution used in these experiments is representative of low surface tension fluids which are used in bioreactors. Comp. Ex. 3 demonstrates that at low pressure, IPA solution breaks through the uncoated substrate. In Comp. Exs. 1 and 2, the onset of break-through held off to the higher pressure of 172 KPa (25 psig). Break-through in these samples was probably caused by incomplete coating of the substrate as evidenced by the low O$_2$/N$_2$ selectivity ratio. In contrast, samples with selectivity ratios higher than 1.4 were able to withstand break through until pressures significantly higher than 172 KPa (25 psig) had been achieved. High selectivities of these samples indicated that the PDD copolymer coating was fully continuous over the surface of the substrate. The high onset pressures of break-through of the operative examples reveal that pressure of a liquid containing dissolved gas in a PDD copolymer membrane unit can be raised considerably to significantly increase the solubility of the dissolved gas. In this way gas migration into the liquid without bubbling and rate of gasification can be enhanced.

Example 17 and Comparative Examples 4–5

The following three types of flat sheet membrane units were prepared: (Ex. 17) a composite membrane unit consisting of a layer of 1 $\mu$m thickness non-porous Polymer A on a 100 $\mu$m thickness Gore-Tex™ expanded polytetrafluoroethylene (e-PTFE) porous layer; (Comp. Ex. 4) a monolithic uncoated 100 $\mu$m e-PTFE porous sheet; and (Comp. Ex. 5) a 1250 $\mu$m thickness monolithic non-porous silicone rubber sheet from Ben-Tech Medical, (California). Each membrane unit included a circularly perforated metal sheet for structural support. Two of each type of supported membrane unit were mounted on opposite sides of a rectangular lollipop-shaped module illustrated schematically in FIG. 3. The membrane units 31 (one shown) were placed in frames 32 to create a complete seal about the perimeter. In the case of the composite membrane unit, the Polymer A-coated side faced outward. The housing 33, frames and membrane units defined an interior chamber, not shown, which was supplied with gas through supply tube 34. Each membrane unit had 65 cm$^2$ surface area 39 exposed through perforations 37 of metal sheet 38 to provide total module effective area for gas permeation of 130 cm$^2$. When pressurized, the silicone rubber sheet membrane unit bulged hemispherically through the perforations of the metal sheet, effectively doubling the module area. After immersing a module into a 5 L reservoir of water, oxygen at the pressure stated in Table III was fed to the supply tube. An agitator in the reservoir was rotated driven at 50 rev. per min. during each trial. Oxygen was thus transferred to the water at the highest rate without bubbling. The dissolved oxygen concentration in water was measured over a period of 30–60 minutes and the initial rate of oxygen transfer is presented in Table III.

TABLE III

| | Description | Oxygen pressure KPa (psig) | O$_2$ Transfer Rate $\left( \dfrac{mL\ O_2/L \times 10^2}{cm^2 \cdot min.} \right)$ |
|---|---|---|---|
| Ex. 17 | 1 $\mu$m Polymer A/100 $\mu$m e-PTFE | 21 (3) | 18.1 |
| Comp. Ex. 4 | 100 $\mu$m e-PTFE | <6.89 (1) | 8.8 |
| Comp. Ex. 5 | 1250 $\mu$m Silicone Rubber | 21 (3) | 5.5 |

Data of Table III shows that a coating of 1 $\mu$m of Polymer A added to e-PTFE substrate improved oxygen delivery rate to water by over 100%. The improvement was apparently aided by the ability to pressurize the gas thereby enhancing the driving force without causing oxygen bubbles in the liquid. At higher than 6.89 KPa (1 psig) pressure, the uncoated e-PTFE membrane admitted so much oxygen that bubbles formed in the water. At the same gas side pressure of 21 KPa (3 psig), the transmission rate of dissolved oxygen through the novel membrane unit also was more than three times the rate through the silicone rubber sheet. It is known that the oxygen flux through a 1 $\mu$m thickness of Polymer A is about 4900 times that through a 1250 $\mu$m thickness of silicone rubber. Thus the observed delivery rate ratio of 3:1 between Ex. 17 and Comp. Ex. 5 indicates that flux was limited by the mass transfer of oxygen in the water. Because thin coatings of PDD copolymers can be incorporated into membrane units which pack to a surface area per unit volume density about eight times that of thick sheet membranes, this example shows that the overall gas flux improvement achievable for oxygenating water by the present invention relative to silicone rubber should be 25–30 fold.

Example 18 and Comparative Example 6

Figure 4:
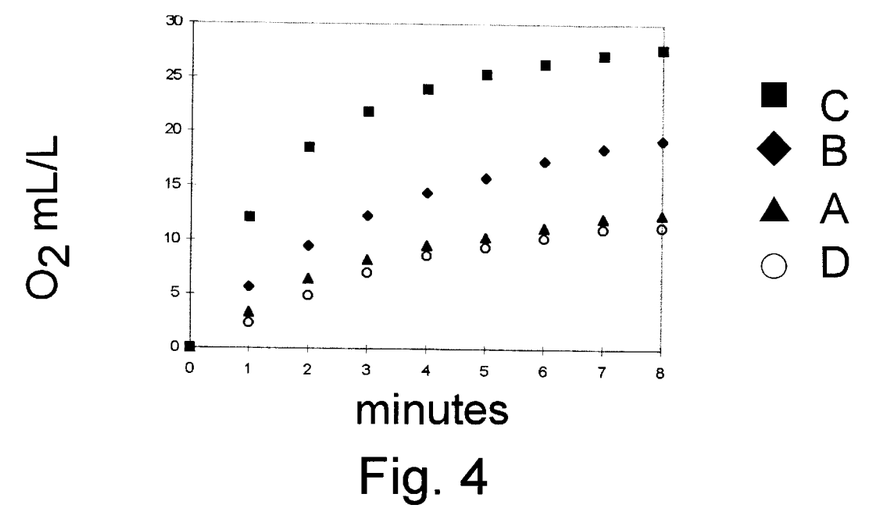
FIG. 4 is a plot of dissolved oxygen concentration in water versus time of water oxygenated at various pressure conditions using a membrane unit of the present invention compared with a conventional membrane unit.

Oxygen was transferred into water using a 1.5 L shell side, water capacity permeator module substantially as shown in FIG. 6. The module employed membrane units of hollow fibers of substrate A coated on the outside surface with Polymer A and having effective area for gas transmission of 50 cm² (Ex. 18). Oxygen was fed on the tube side at 34.5 KPa (5 psig) and water at about 26–28° C. was passed through the shell side at 0.5 L/min. The dissolved oxygen concentration was measured each minute up to 8 minutes. The data are identified as points "A" plotted in FIG. 4 as concentration of oxygen in water vs. time. The experiment was repeated at 69 KPa (10 psig) (points "B") and 138 KPa (20 psig) (points "C"). Oxygen delivery to water through a 150 μm thickness 50 cm² area microporous polyvinylidene fluoride ("PVDF") membrane at 34.5 KPa (5 psig) (Comp. Ex. 6) was measured for comparison. The results are plotted as points "D" in FIG. 4. The figure illustrates that oxygen transmission rate according to the novel method was equivalent to that of PVDF, a hydrophobic, microporous polymer. Additionally, it is seen that oxygen transmission rate without bubbling afforded by the novel method can be dramatically increased by increasing tube side pressure.

Examples 19–20 and Comparative Examples 7–8

High oxygen demanding, Sf-21 cells at a density of about 250×10³ cells/mL were placed in Cyto-Sf-9 culture medium (Kemp Biotechnologies, Inc.) in a 5L bioreactor at 27° C. Oxygen demand for these cells was experimentally measured to be about $10^{-10}$ mL/(min-cell). For 5–7 days oxygen was fed to the culture medium through a 130 cm² area flat sheet membrane unit of 1 μm thickness Polymer A coated on 100 μm thick, 0.05 μm microporous expanded polytetrafluoroethylene substrate at a gas rate effective to provide 50% of saturation. The Polymer A coated side of the membrane unit was exposed to the culture medium. The reactor was sampled daily for cell density and viability. Viability was determined by mixing a cell population sample of selected dilution with 0.4% aqueous Trypan Blue dye and counting unstained (viable) and total cells with a hemocytometer. In all cases, viability was at least 90%. The culture was allowed to propagate until the fail point at which the supplied oxygen was unable to satisfy demand. Subsequently the dissolved oxygen concentration declined to zero and the culture was terminated. The peak cell density was calculated at the fail point. In both of duplicate determinations, Ex. 19–20, the peak cell density was 2.7×10⁶ cells/mL indicating that 2.1×10⁴ cells/(mL·cm²) can be supported by oxygen transmitted through the novel membrane unit at test conditions.

The experiment was repeated in duplicate (Comp. Exs. 7–8) with the membrane unit replaced by 260 cm² flat sheet of 1250 μm thick silicone rubber. Fail point peak cell densities of 1.7×10⁶ cells/mL and 1.2×10⁶ cells/mL were observed. These values calculate to 0.7×10⁴ and 0.5×10⁴ cells/(mL·cm²) supportable cells per unit membrane area, respectively, and averaging 0.6×10⁴ cells/(mL·cm²). These examples show that the method according to the present invention can support 3.5 times the cell density per unit area as silicone rubber. This result is consistent with the results of Examples 17 and Comp. Exs. 4–5.

Example 21

The novel membrane unit was shown to be non-adhesive to cells in culture as follows. Vero cells, an established attachment dependent cell line derived from African Green Monkey kidney, was seeded into a T-75 cell culture flask containing 50/50 DMEM/F12 (10% FBS) cell culture medium. A piece of membrane unit consisting of 1 μm layer of Polymer A coated on 100 μm layer of e-PTFE was steam sterilized and placed in the flask. Cells were permitted to propagate to confluence on the glass of the flask and in contact with the membrane unit. At near-confluence, the membrane was transferred to a petri dish, washed with 1× phosphate buffered saline (PBS) and stained with 1% Neutral Red dye. The culture flask was similarly drained, rinsed and stained. One minute after staining, both the membrane and culture flask were rinsed carefully with PBS. The membrane rinsed clear of color indicating no attachment of cells to the membrane material, however, the glass on the floor of the flasks remained red, revealing that the cells had adhered to the flask. This example demonstrates that bioreactor mass should not attach to perfluoro-2,2-dimethyl-1,3-dioxole copolymers, and therefore the material should provide durable service in bioreactor utility.

Example 22 and Comparative Example 9

Figure 3:
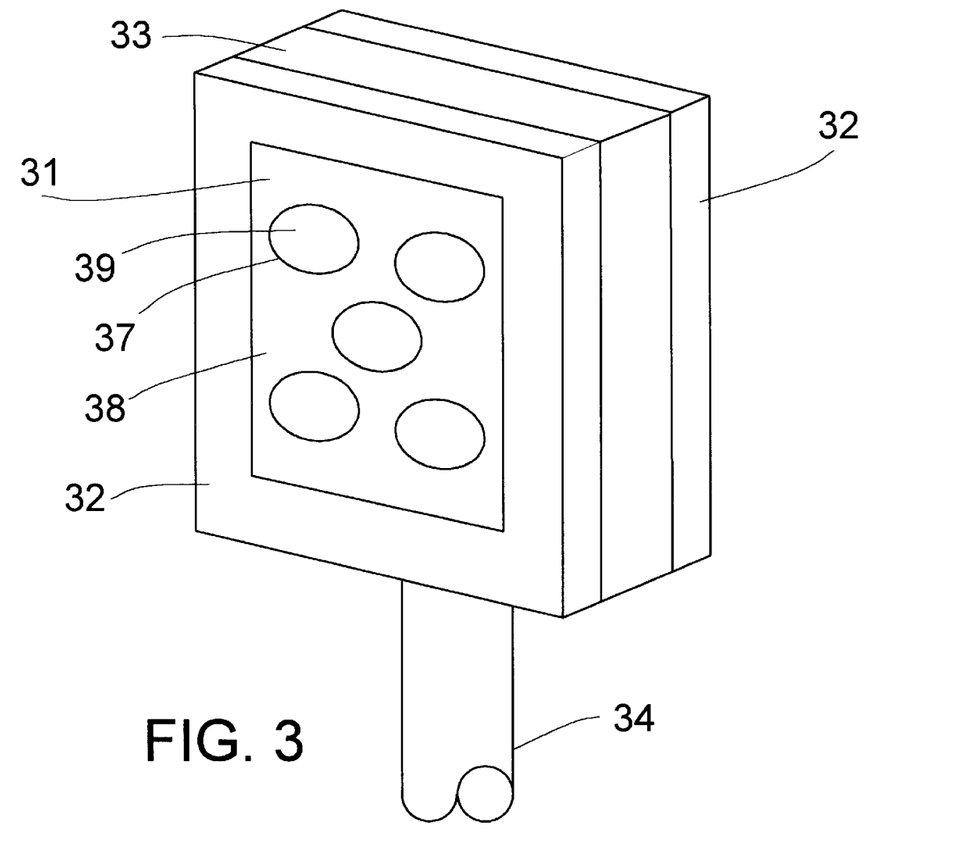
FIG. 3 is a schematic illustration of a flat membrane unit, permeator module for use with the present invention.
Figure 5:
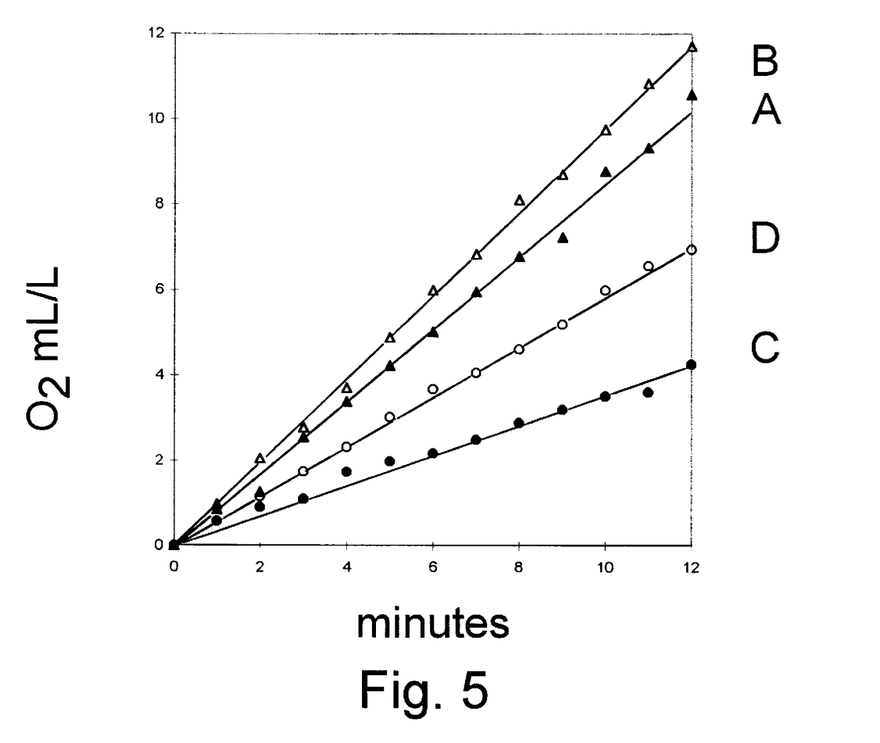
FIG. 5 is a plot of dissolved oxygen concentration in water versus time during oxygenation of a bioreactor for the process of the present invention compared with a conventional process.

A 130 cm² membrane unit of 1 μm thick layer of Polymer A coated on a 100 μm thick layer of 0.05 μm microporous e-PTFE substrate was mounted on a permeator module substantially as shown in FIG. 3. The module was used to oxygenate three successive Sf-21 cell cultures until each cell population peaked as indicated by a drop in oxygen concentration. Each oxygenation lasted about 5–7 days. After these oxygenations, the ability of the membrane unit to transfer oxygen was then determined by immersing the module in a water bath and adding oxygen. The dissolved oxygen concentration in the bath was recorded periodically and the results are plotted in FIG. 5 as line "A". Subsequently, the membrane structure was washed with Tergizyme™ and the water bath oxygenation measurements were repeated. Results are plotted as line "B" in FIG. 5. These procedures were duplicated except that a 1250 μm thick membrane of silicone rubber (Comp. Ex. 9) was used instead of the Polymer A/e-PTFE substrate. The prewash and post wash data are plotted in FIG. 5 as lines "C" and "D", respectively.

Slopes of lines A–D indicate the oxygen transmission rate of the membrane support structures. In cleaned and fouled conditions, the novel membrane unit oxygen transmission rates were 0.995 and 0.893 mL/(L·min.), respectively, showing only a 10% oxygen transmission rate loss due to fouling. The clean and fouled oxygen transmission rates for the silicone rubber membrane unit were 0.600 and 0.349, respectively. The silicone rubber suffered a substantial oxygen transmission rate loss of 42% which suggests that the novel membrane unit is much more suitable for bioreactor processing than conventional material. In addition, the oxygen transmission rate of the Polymer A-coated membrane unit was much greater than the silicone rubber in both cleaned and fouled conditions. Even in fouled condition, the membrane unit of this invention yielded a 49% higher transmission rate than the cleaned silicone rubber membrane.

Example 23 and Comparative Example 10

A permeator module of the type shown in FIG. 6 was equipped with 53 PVDF hollow fibers coated on the inside surface with a 0.5 μm thick layer of Polymer A (Ex. 23). The PVDF hollow fibers had an inside diameter of 1 mm and were 11.94 cm long, which furnished the module with 200 cm² mass transfer area. Initially deoxygenated water in a 56.8 L sealed tank was recirculated through the tube side of the permeator module via first fluid inlet and outlet ports at the flow rate shown in Table IV. Air at 103 KPa (15 psig) was fed to the shell side through second fluid inlet port. The second fluid outlet port was capped shut. Concentration of oxygen dissolved in the water was measured periodically using a YSI model 55 dissolved oxygen meter. Dissolved oxygen concentration was measured periodically. At two levels of dissolved oxygen, more specifically, at 1–2 and 5–6 parts per million (ppm), the oxygen transfer rate ("OTR") was calculated from the dissolved oxygen vs. time measurements. The water was replaced with deoxygenated water and the procedure was rerun without changing the permeator module. The low and high dissolved oxygen level OTRs were calculated as before. These OTRs are reported in Table IV.

A permeator module was prepared identically to that of Ex. 23 except that the PVDF hollow fibers were not coated (Comp. Ex. 10). Two consecutive oxygenation runs were carried out as in Ex. 23. The results are shown in Table IV.

The first run OTRs at each of the high and low dissolved oxygen levels of Ex. 23 and Comp. Ex. 10 show that the initial oxygen transmission rate with a PDD copolymer-coated membrane unit is at least equivalent to that of a conventional membrane unit. Comparison of the first and second run OTRs in each series shows that the OTR remained stable for the PDD-copolymer-coated hollow fibers. At the high dissolved oxygen level, the OTR increased in the second run. The uncoated PVDF membrane unit runs indicate that at each level of dissolved oxygen, the OTR dropped approximately in half from the first to the second run. This demonstrates an improved stability of flux according to the novel method.

TABLE IV

|  | Water Recirculation Flow (L/min.) | OTR kg/h (lbs/h) × $10^6$ at 1–2 ppm | OTR kg/h (lbs/h) × $10^6$ at 5–6 ppm |
| --- | --- | --- | --- |
| Ex. 23 |  |  |  |
| run 1 | 5.8 | 363 (800) | 179 (395) |
| run 2 | 5.8 | 338 (745) | 238 (525) |
| Comp. Ex. 10 |  |  |  |
| run 1 | 7.2 | 254 (560) | 172 (380) |
| run 2 | 7.5 | 166 (365) | 86.2 (190) |

Example 24

A permeator module of the type shown in FIG. 6 was constructed from 5,952 polypropylene hollow fibers of 200 µm inside diameter and 21.5 cm length. The inside surface of each fiber was coated with a 1.0 µm thick layer of Polymer A to provide 8,035 cm² effective mass transfer area. Water with 6.44 ppm initial dissolved oxygen concentration was recirculated through the air-tight tank used in Ex. 23 and the tube side of the module at 19° C. The shell side of the module was maintained under vacuum of −101 KPa (30 inch Hg vacuum). Dissolved oxygen concentration was measured periodically with a model 55 YSI dissolved oxygen meter and the OTR was calculated therefrom. The data shown in Table V validate the ability of the PDD-copolymer coated membrane unit to degasify a liquid.

TABLE V

| Time min. | Dissolved Oxygen Conc. ppm | OTR kg/h (lbs/h) × $10^6$ | Recirculation Flow Rate L/min. |
| --- | --- | --- | --- |
| 0 | 6.44 | — | 5.0 |
| 5 | 6.02 | 286.0 (630.5) |  |
| 10 | 5.59 | 292.8 (645.5) |  |
| 15 | 5.20 | 265.6 (585.5) |  |
| 20 | 4.80 | 272.4 (600.5) |  |
| 25 | 4.43 | 251.9 (555.4) | 4.29 |
| 30 | 4.27 | 109.0 (240.2) |  |
| 35 | 3.98 | 197.4 (435.3) |  |
| 40 | 3.82 | 109.0 (240.2) |  |
| 45 | 3.59 | 156.6 (345.3) |  |
| 50 | 3.46 | 88.5 (195.2) |  |
| 60 | 3.1 | 122.6 (270.2) |  |
| 70 | 2.8 | 102.2 (225.2) | 4.0 |
| 80 | 2.49 | 105.6 (232.7) |  |
| 85 | 2.41 | 54.5 (120.1) |  |

Although specific forms of the invention have been selected for illustration in the drawings and examples, and the preceding description is drawn in specific terms for the purpose of describing these forms of the invention, this description is not intended to limit the scope of the invention which is defined in the claims.

What is claimed is:

1. A method of transferring a gaseous component between two fluids having different partial pressures of the gaseous component, and wherein at least one of the two fluids is a liquid, the method comprising:

contacting one of the two fluids with a first side of a two-sided, membrane unit, the membrane unit including a nonporous membrane (i) being substantially impermeable to the liquid and having a permeability to oxygen of at least 100 barrers; (ii) formed from an amorphous copolymer of perfluoro-2,2-dimethyl-1,3-dioxole; and (iii) being at a temperature below the glass transition temperature of the amorphous copolymer; wherein the nonporous membrane has an oxygen/nitrogen selectivity of at least about 1.5, and simultaneously contacting the second side of the two-sided, membrane unit with the other of the two fluids.

2. The invention of claim 1 wherein the second fluid is in the gaseous state.

3. The invention of claim 2 wherein the partial pressure of the gaseous component in the second fluid is higher than the partial pressure of the gaseous component in the liquid.

4. The invention of claim 2 wherein the partial pressure of the gaseous component in the second fluid is lower than the partial pressure of the gaseous component in the liquid.

5. The invention of claim 1 wherein the membrane unit further includes a substrate means for structurally supporting the membrane, the substrate means being affixed coextensively to one side of the membrane and having a face opposite to the second side the membrane.

6. The invention of claim 5 wherein the substrate means is selected from the group consisting of a perforated sheet; a porous woven fabric; a monolithic microporous polymer film and a microporous, hollow fiber.

7. The invention of claim 6 wherein the membrane unit is a hollow fiber.

8. The invention of claim 5 wherein the liquid is in contact with the second side of the membrane.

9. The invention of claim 8 wherein both fluids are liquids and the membrane unit further includes a second nonporous membrane affixed coextensively to the face of the substrate means, the second membrane (i) being substantially impermeable to the liquid and having a permeability to oxygen of at least 100 barrers; (ii) formed from an amorphous copolymer of perfluoro-2,2-dimethyl-1,3-dioxole; and (iii) being at a temperature below the glass transition temperature of the copolymer, and wherein the second nonporous membrane has an oxygen/nitrogen selectivity of at least about 1.5.

10. The invention of claim 5 wherein a pressure difference between the two fluids is maintained.

11. The invention of claim 10 wherein the pressure difference is at least 34.5 KPa.

12. The invention of claim 11 wherein the pressure difference is at least 69 KPa.

13. The invention of claim 10 wherein the second fluid is in the gaseous state.

14. The invention of claim 13 wherein pressure of the liquid is at least 34.5 KPa higher than the pressure of the second fluid.

15. The invention of claim 2 wherein the gaseous component is selected from the group consisting of elemental gases; hydrocarbons; halocarbons; halohydrocarbons; and nitrous oxide; carbon dioxide; ozone; hydrogen sulfide; ammonia; sulfur dioxide; carbon monoxide; phosgene and any mixture of any of them.

16. The invention of claim 15 wherein the gaseous component is an oxygen containing compound selected from the group consisting of oxygen, ozone, carbon monoxide, carbon dioxide, sulfur dioxide and a mixture of them.

17. The invention of claim 16 wherein the gaseous component is oxygen.

18. The invention of claim 16 wherein the gaseous component is a mixture selected from the group consisting of oxygen/ozone, oxygen/nitrogen and oxygen/nitrogen/ozone.

19. The invention of claim 1 wherein the amorphous copolymer is a copolymer of perfluoro-2,2-dimethyl-1,3-dioxole and a complementary amount of at least one monomer selected from the group consisting of tetrafluoroethylene, perfluoromethyl vinyl ether, vinylidene fluoride, hexafluoropropylene and chlorotrifluoroethylene.

20. The invention of claim 19 wherein the amorphous copolymer is a dipolymer of perfluoro-2,2-dimethyl-1,3-dioxole and tetrafluoroethylene.

21. The invention of claim 20 wherein the dipolymer comprises 50–95 mole % polymerized perfluoro-2,2-dimethyl-1,3-dioxole.

22. The invention of claim 1 wherein the amorphous copolymer has a glass transition temperature of at least 115° C.

23. The invention of claim 1 wherein the membrane has a permeability to oxygen of at least 200 barrers.

24. The invention of claim 23 wherein the membrane has a permeability to oxygen of at least 500 barrers.

25. The invention of claim 3 wherein the liquid is selected from the group of water, aqueous solutions and aqueous dispersions.

26. A method of using a membrane unit to transfer a gaseous component between a liquid and a fluid comprising simultaneously contacting a first side of the membrane unit with the liquid and a second side of the membrane unit with the fluid, wherein the membrane unit includes a nonporous membrane that is (i) substantially impermeable to the liquid and having a permeability to oxygen of at least 100 barrers; (ii) formed from an amorphous copolymer of perfluoro-2,2-dimethyl-1,3-dioxole; and (iii) at a temperature below the glass transition temperature of the amorphous copolymer; wherein the nonporous membrane has an oxygen/nitrogen selectivity of at least about 1.5, and wherein the gaseous component is present in the liquid at a concentration defined by a partial pressure and is present in the fluid at a concentration defined by a different partial pressure.

27. The invention of claim 26 wherein the use is ozonating waste water.

28. The invention of claim 26 wherein the use is oxygenating natural bodies of water.

29. The invention of claim 26 wherein the use is oxygenating water in aquaculture tanks and ponds.

30. The invention of claim 26 wherein the use is depleting oxygen in anaerobic reactors.

31. The invention of claim 26 wherein the use is depleting oxygen of boiler water feed.

32. The invention of claim 3 wherein the liquid is free of the gaseous component in the gaseous state.

* * * * *

UNITED STATES PATENT AND TRADEMARK OFFICE
CERTIFICATE OF CORRECTION

PATENT NO. : 5,876,604  Page 1 of 1
DATED : March 2, 1999
INVENTOR(S) : Stuart Nemser et al.

It is certified that error appears in the above-identified patent and that said Letters Patent is hereby corrected as shown below:

Column 1,
Before "FIELD OF THE INVENTION" insert the following paragraph:
-- This invention was made with Government support under contract number R43 GM 54385 awarded by the National Institute of Health. The Government has certain rights in the invention. --

Signed and Sealed this

Twenty-fifth Day of December, 2001

Attest:

JAMES E. ROGAN
Attesting Officer  Director of the United States Patent and Trademark Office